United States Patent
Di Girolamo et al.

(10) Patent No.: US 9,339,444 B2
(45) Date of Patent: May 17, 2016

(54) CERAMIC IMPLANT

(71) Applicant: Z-Systems Schweiz AG, Oensingen (CH)

(72) Inventors: Rubino Di Girolamo, Oberageri (CH); Thomas Hug, Erlenbach (CH)

(73) Assignee: Z-SYSTEMS SCHWEIZ AG, Oensingen (CH)

( * ) Notice: Subject to any disclaimer, the term of this patent is extended or adjusted under 35 U.S.C. 154(b) by 0 days.

(21) Appl. No.: 13/920,646

(22) Filed: Jun. 18, 2013

(65) Prior Publication Data
US 2014/0030676 A1 Jan. 30, 2014

(30) Foreign Application Priority Data

Jun. 20, 2012 (CH) .......................... 868/12

(51) Int. Cl.
A61C 8/00 (2006.01)
A61K 6/02 (2006.01)

(52) U.S. Cl.
CPC .............. A61K 6/024 (2013.01); A61C 8/0012 (2013.01); A61C 8/0022 (2013.01); A61C 8/0062 (2013.01); A61C 8/0075 (2013.01); A61C 8/0089 (2013.01); *A61C 8/006* (2013.01)

(58) Field of Classification Search
CPC ................. A61C 8/00; A61C 8/0004; A61C 8/005–8/0063; A61C 8/0066; A61C 8/0069; A61C 8/0071; A61C 8/0075; A61C 8/0078; A61C 8/0089; A61C 2008/00; A61C 2008/0018; A61C 2008/0037; A61C 2008/0046
USPC ....................................... 433/172–176, 201.1
See application file for complete search history.

(56) References Cited

U.S. PATENT DOCUMENTS

| | | | | | |
|---|---|---|---|---|---|
| 5,246,370 | A | * | 9/1993 | Coatoam | A61C 8/00 433/173 |
| 5,759,034 | A | * | 6/1998 | Daftary | A61C 8/0018 433/172 |
| 5,785,525 | A | * | 7/1998 | Weissman | A61C 8/0018 433/174 |
| 6,039,568 | A | * | 3/2000 | Hinds | A61C 8/0036 433/173 |
| 6,312,258 | B1 | * | 11/2001 | Ashman | 433/172 |
| 6,854,972 | B1 | * | 2/2005 | Elian | A61C 8/0006 433/173 |
| 7,179,088 | B2 | * | 2/2007 | Schulter et al. | 433/173 |
| 7,827,694 | B2 | * | 11/2010 | Soler et al. | 29/896.1 |
| 8,449,297 | B2 | * | 5/2013 | Boehm-Van Diggelen | A61C 8/001 433/173 |
| 2004/0166476 | A1 | * | 8/2004 | Weissman | 433/173 |
| 2006/0078847 | A1 | | 4/2006 | Kwan | |
| 2010/0240009 | A1 | * | 9/2010 | Gogarnoiu | 433/173 |

FOREIGN PATENT DOCUMENTS

EP 0092209 10/1983
FR 2571607 4/1986

* cited by examiner

*Primary Examiner* — Ralph Lewis
(74) *Attorney, Agent, or Firm* — Rankin, Hill & Clark LLP

(57) ABSTRACT

A single-piece ceramic dental implant is provided, with a distal enossal threaded region, a gingival intermediate region and a proximal region. A thread is arranged in the threaded region and has a core radius and an outer radius of the thread. A proximally accessible insertion geometry for screwing the threaded region into a bone tissue is arranged in the intermediate region, wherein the insertion geometry is designed as a non-rotationally-symmetrical outer structure. The proximal region includes at least one structure for fastening a single-part or multi-part attachment element. An implant diameter in every section perpendicular to the implant axis, in the intermediate region is equal to or larger than the double of the core radius of the thread. Thus each implant diameter through the insertion geometry is equal to or larger than the double of the core radius of the thread.

20 Claims, 6 Drawing Sheets

CERAMIC IMPLANT

BACKGROUND OF THE INVENTION

1. Field of the Invention

The invention lies in the field of medical technology and relates to a dental implant, in particular to a single-piece ceramic implant, a ceramic implant system as well as a dental implant system and a set with a ceramic implant.

2. Description of Related Art

Ceramic implants and in particular ceramic implants consisting of ceramic based on zirconium oxide have various advantages compared to the known titanium implants. They have an excellent biocompatibility, since ceramic and in particular ceramic based on zirconium oxide rarely trigger physiological reactions and in particular trigger no allergic reactions. Metal-free ceramic implants are therefore suitable for allergy sufferers. Moreover, the optimal tissue compatibility of ceramic implants effects a very rapid gum attachment onto freshly implanted dental implants. Thus improved aesthetics compared to the traditional titanium implants result, also thanks to the white colour of the zirconium oxide ceramic. The good in-growth into the gums is also maintained over the longer term, since less plaque attaches to the ceramic implants and thus gum inflammation and gum recession disease occur to a lesser extent.

However, compared to titanium implants, ceramic implants have the disadvantage that ceramic material, in particular oxide ceramic such as ceramic based on zirconium oxide or ceramic based on aluminium oxide is a brittle material. Thus it is a challenge to overcome the comparatively high proneness to breakage of the ceramic material, even if for example yttrium-stabilised ceramic based on zirconium oxide already has an improved breakage stability. The technical design of ceramic implants must therefore be matched to the brittle material properties. A single-part implant system is less prone to breakage than a two-part implant system.

Many dental implants, ceramic implants and other implants are screwed into the jawbone. All implants screwed into the jawbone, whether single-part of two-part, are screwed into the bone by way of an insertion tool being applied onto the insertion geometry of the implant and a screw-in moment being transmitted onto the implant. The implant is damaged if this force effect overloads the comparatively low breakage stability of the ceramic implant. It is particularly with an inner connection in ceramic that the danger of breakage exists with screw-in forces which lie in the upper region of a commonly applied torque of approx. 35 to 70 Ncm. Implant breakages, with which ceramic pieces can also detach from the implant, increase the risk of complication with regard to dental surgery, and the wear of ceramic implants.

BRIEF SUMMARY OF THE INVENTION

It is the object of the present invention, to overcome these disadvantages in the state of the art, and to provide a ceramic implant which has an improved breakage stability itself and onto which a greater screw-in moment can therefore be applied.

This object is achieved by a single-piece ceramic implant with a distal enossal thread region, a gingival intermediate region and a proximal region. A thread with a core radius and an outer radius of the thread is arranged in the threaded region. A proximally accessible insertion geometry for screwing the threaded region into a bone tissue is arranged in the intermediate region, wherein the insertion geometry is designed as a non-rotationally-symmetrical outer structure. The proximal region comprises at least one structure for fastening a single-part or multi-part attachment element. In the intermediate region, an implant diameter in every section perpendicular to the implant axis is at least equal to the double of the core radius of the thread.

Thus also every implant diameter through the insertion geometry is at least equal to the double of the core radius of the thread.

In the present text, a ceramic implant is indicated as a single-piece ceramic dental implant which consists of ceramic material, in particular of an oxide ceramic such as ceramic based on zirconium oxide, in particular yttrium-stabilised ceramic based on zirconium oxide or ceramic based on aluminium oxide.

The axial positioning of a region or of a structure in this application is characterised by the terms distal and proximal with respect to the implantation direction, such that the distal direction corresponds to the direction to the apical end of the dental implant (or of a tooth) and the proximal direction corresponds to the coronal direction of the dental implant (or of a tooth).

The proximal region of the ceramic implant, like an abutment of a two-piece implant, serves in particular for receiving and fastening a single-part or multi-part attachment element. The proximal region therefore comprises at least one structure, on which and/or by way of which an attachment element is fastened on the ceramic implant. Exemplary structures are a conical or cylindrical stem or a lockball.

The intermediate region of the ceramic implant comprises the insertion geometry which is arranged at the proximal end of the intermediate region. The proximal end of the intermediate region or the distal end of the proximal region corresponds anatomically essentially to the gum passage region. The intermediate region of the ceramic implant which in some embodiments comprises a widening zone and/or a distancing zone distally of the insertion geometry, is surrounded essentially over its complete axial length by gum (gingiva). The ceramic implant is suitable for different gingiva heights, depending on the axial length of the intermediate region. The axial length of the intermediate region for example has a dimension of between 1.5 and 5.5 mm, for example 2.5 mm, 3.5 mm or 4.5 mm.

The enossal threaded region of the ceramic implant is arranged distally of the intermediate region and serves for anchoring the ceramic implant in the bone. The proximal end of the thread or in some embodiments the proximal end of the thread run-out defines the proximal end of the threaded region and simultaneously also the distal end of the intermediate region.

In the present text, the distance between the implant axis and the implant surface perpendicular to the axis is indicated as the implant radius. In regions of the implant with a non-circular cross section, in particular relating to the non-rotationally-symmetrical insertion geometry, the smallest implant radius is defined as the inner radius and it corresponds to the smallest distance between the implant axis and the implant surface perpendicular to the axis. Analogously, the greatest implant radius is defined as the outer radius and it corresponds to the greatest distance between the implant axis and the implant surface perpendicular to the axis. The smallest diameter of a section perpendicular to the implant axis of the implant is defined as the shortest connection path between two points on the implant surface, said path leading through the implant axis. With a regular even-numbered outer polygon, i.e. outer hexagon, the smallest implant diameter corresponds to the double of the inner radius.

Generally, if not stated otherwise, the implant diameter in the present text is defined as the average diameter of a section perpendicular to the axis. The implant diameter in the case of a circular section is the circle diameter. In the case of a non-circular section perpendicular to the implant axis, i.e. for example a section through the insertion geometry in the intermediate region of the implant, the implant diameter is the circle diameter of that circle with a middle point on the implant axis and which has an equally large area as the non-circular section through the implant. The smallest or greatest implant diameter in an axial region of the implant, for example in the intermediate region, in the region of the insertion geometry or in the threaded region is thus the smallest or greatest value of the average diameter of all sections perpendicular to the implant axis in this region. The implant diameter of the ceramic implant at the proximal end of the thread for example has a length of 3 mm to 4.5 mm, in particular 3.5 mm to 4.0 mm.

The core radius of the thread in the present text is defined as the inner radius of the thread at the proximal end of the thread. The core diameter is defined as the double of the core radius at the proximal end of the thread. In some embodiments, a thread run-out is arranged proximally to the proximal end of the thread. In some embodiments of the thread run-out, the core radius increases in the proximal direction whereas the outer radius of the thread remains unchanged. The outer radius of the thread and of the thread run-out is the largest radius of the thread at the proximal end of the thread.

The size of the smallest implant diameter of the implant is a factor which substantially co-determines the breaking strength of the ceramic implant. Generally, it is the case that the greater the smallest implant diameter of the implant and in particular the smallest implant diameter in the region of the insertion geometry, the less prone to breakage is the ceramic implant. A big advantage of the ceramic implants according to the invention is the fact that the smallest diameter of the insertion geometry is not smaller than the core diameter of the thread and thus the breakage strength of the ceramic implant according to the invention is increased compared to known ceramic implants.

The inner radius of the non-rotationally-symmetrical outer structure of the insertion geometry indicates the smallest distance between the implant axis and the implant surface perpendicular to the axis. The outer radius of the non-rotationally-symmetrical outer structure of the insertion geometry indicates the greatest distance between the implant axis and the implant surface perpendicular to the axis. In some embodiments of the ceramic implant, the insertion geometry has an inner radius which is equally large or larger than the core radius of the thread.

In some embodiments of the ceramic implant, the difference between the outer radius and the inner radius of the outer structure of the insertion geometry is small, in particular smaller than 0.3 mm or 0.2 mm, and for example has a magnitude in a region between 0.1 mm or 0.15 mm as a lower limit and 0.16 or 1.8 as an upper limit and in particular measures between 0.13 mm and 0.18, for example 0.15 mm. An almost round shape of the non-rotationally-symmetrical outer structure and in particular convex outer structure of the insertion geometry lie close to an anatomical shape.

In some embodiments of the ceramic implant, the outer radius of the insertion geometry is at least as large as the outer radius of the thread.

In some embodiments, the intermediate region of the ceramic implant additionally to the insertion geometry comprises a widening zone and/or a distancing zone. The widening zone is arranged distally of the insertion geometry and proximally of the threaded region and in some embodiments it is directly adjacent the proximal end of the threaded region, in particular directly adjacent the thread or the thread run-out. The implant diameter at the distal end of the widening zone in some embodiments is equal to and in other embodiments is larger than the double of the outer radius of the thread and it widens in the widening zone in the proximal direction. The implant diameter at the proximal end of the widening zone is greater than at its distal end. The widening zone in some embodiments is designed as a tulip-like extension which projects in an S-curve.

The widening zone is suitable for increasing the implant diameter in the proximal direction in the intermediate region. With some embodiments of implants, for example with a relatively small implant diameter in the threaded region, the implant diameter in the widening zone increases in the proximal direction. Sets of ceramic implants with a different thread diameter and whose screw-in geometries have non-rotationally-symmetrical outer structures with identical dimensions such as for example the same inner and outer radii of a curve of constant width, can be provided in this manner.

In some embodiments, the widening zone of the intermediate region is distanced to the thread, which means to say that the implant diameter does not widen directly proximally to the thread but the intermediate region has a distancing zone. The distancing zone in embodiments with a widening zone is arranged between the proximal end of the threaded region and the distal end of the widening zone or in embodiments without a widening zone is arranged between the proximal end of the threaded region and the distal end of the insertion geometry. In the distancing zone, the implant radius is at least equal to or larger than the core radius of the thread and is essentially equal to the outer radius of the thread or the thread run-out and in particular the implant radius is equal to the outer radius of the thread or of the thread run-out.

In some embodiments of the ceramic implant with a widening zone, the outer radius of the insertion geometry at the most is equal to an outer radius of the in particular tulip-shaped widening zone at its proximal end.

In some embodiments, the implant diameter of the insertion geometry is somewhat smaller than the implant diameter at the proximal end of the widening zone, for example less than 0.3 mm or 0.2 mm smaller and in particular between 0.13 mm and 0.18 mm smaller, but the implant diameter in the complete intermediate region, thus also every implant diameter through the insertion geometry is equal to or larger than the core diameter of the thread.

In some embodiments, the implant diameter at the proximal end of the widening zone measures at least 125%, in particular at least 150%, 175%, 200% or 225% of the implant diameter at the proximal end of the threaded region. In contrast to the ceramic implants described above, with ceramic implants which are known from the state of the art, the insertion geometry is arranged in the proximal region and not in the intermediate region. For this reason, these known ceramic implants have a comparatively smaller implant diameter in the region of the insertion geometry as well as a greater proneness to breakage.

A big advantage of the arrangement of the proximally accessible insertion geometry in the intermediate region, in which each implant diameter is at least as equal to the core diameter in the threaded region, is the increased distance of the insertion geometry to the implant axis. A certain force which is applied onto the insertion geometry of a ceramic implant according to the invention creates a greater torque than an equally large force if it were to be applied onto a conventional implant, whose insertion geometry has a smaller distance to the implant axis. By way of increasing the distance of the insertion geometry to the implant axis, a comparatively smaller force effects a sufficiently high torque, in order to screw the implant into the bone, and loads the brittle ceramic material of the implant to a lesser extent. This reduces the proneness to breakage of the ceramic implant according to the invention.

The reduction of the breakage risk due to the inventive arrangement of the insertion geometry in the intermediate region with a dimensioning of the implant diameter such that it is at least equal to the greatest thread diameter, has been found to be particularly advantageous with ceramic implants with a self-cutting thread. This is because an increased force must be applied onto the insertion geometry of the implant with a self-cutting thread, in order to screw the implant into the bone tissue, compared to screwing in an implant into a threaded bore which has been pre-drilled into the bone tissue. For this reason it is particularly conventional ceramic implants with a self-cutting thread which are prone to breakage.

A further big advantage of the arrangement of the insertion geometry in the intermediate region is that this remains unaffected should the implant in the proximal region be ground or should it break, and therefore is still present, in order to screw the implant out of the bone in the case that it has to be removed.

A further advantage of the arrangement of the insertion geometry closer to the proximal end of the threaded region arises on account of a very fine but visible line on the implant surface at the border between the thread and the insertion geometry or to the widening zone or distancing zone. This represents an implant aid for the dental surgeon. This is the case even with a very anatomical design of the non-rotationally-symmetrical outer structure, which for example is designed as an almost round, concave pentagonal curve of equal width, and which for example is set back or projects, in the range of less than 3 mm, in particular less than 2 mm.

A further advantage of the arrangement of the proximally accessible insertion geometry in the intermediate region, is the shifting of the insertion geometry in the distal direction, so that additional degrees of freedom are obtained for the technical design, such as the design of the shape and surface, of the proximal region and thus for the design of the at least one structure for fastening the attachment element. For example, the axial length of the proximal region can be comparatively shorter than in ceramic implants from the state of the art, since the insertion geometry is not also arranged in this proximal region. The selection of the shape and the technical design of the proximal region are essentially independent of the further distally arranged insertion geometry. This increases the adaptation possibilities of the proximal region to parameters demanded by the attachment element.

A further advantage of the arrangement of the insertion geometry in the intermediate region is the possibility is providing a single insertion geometry with a constant shape and size for a number of different ceramic implants as a ceramic implant system. Due to the arrangement of the insertion geometry in the intermediate region, its design and its implant diameter can be selected independently of the design of the proximal region and the at least one structure thereof which is for fastening the attachment element, and also independently of the implant diameter in the distal, enossal region.

A further aspect of the invention thus relates to a ceramic implant system with at least two ceramic implants, wherein these ceramic implants are equipped with an equal, non-rotationally-symmetrical outer geometry of the insertion geometry. An equal, non-rotationally-symmetrical outer structure means that the outer structure is functionally equal, which is to say that it functionally cooperates with a structurally identical insertion tool such that by way of applying the tool, a torque can be transmitted onto the ceramic implant and it can be rotated into the bone for example. In some embodiments of equal non-rotationally-symmetrical outer geometry, the sections of the insertion geometry perpendicular to the implant axis are congruent. Some embodiments of the ceramic implant system additionally comprise an insertion tool which cooperates with the functionally equal outer structure of the insertion geometry.

Thus some embodiments of the ceramic implant system comprise at least two ceramic implants with an equal, in the sense of functionally equal, insertion geometry or in particular with an identical shape and size of the insertion geometry, with which for example the proximal region of these ceramic implants differs for example with respect to the axial length or the implant diameter or by way of the proximal region being provided with males for different female systems. In further embodiments of the ceramic implant system, the ceramic implants alternatively or additionally differ in the threaded region and for example have different axial lengths or implant diameter of the threaded region, in particular a different outer diameter of the thread at the proximal end of this. In some embodiments, the insertion geometry with an equal outer geometry in the sense of the functionally equal outer geometry described above, has a different axial length. Thus the ceramic implants of a ceramic implant system alternatively or additionally to differences in the proximal region and/or in the threaded region, also differ in the intermediate region, as mentioned above for example in the axial length of the insertion geometry or for example additionally or alternatively in the presence or the design of the optional widening zone and/or the distancing zone.

Advantageously, only a single insertion tool must be provided for a ceramic implant system comprising a plurality of ceramic implants, and this tool cooperates with such a functionally equal insertion geometry, in particular of an identical shape and size for different embodiments of the ceramic implant or for a complete ceramic implant system with a plurality of ceramic implants.

The insertion geometry of single-part ceramic implants which is arranged in the intermediate region is typically an outer structure. Common screw-in geometries are outer polygon profiles, in particular an outer hexagon or an outer octagon or an outer bi-hexagon. When screwing an implant into the bone by way of an outer geometry, no tensile forces arise in the implant in contrast to screwing-in by way of inner geometry. Such tensile forces in the implant typically arise due to the pressing of a screw-in instrument into an inner geometry, and the brittle ceramic material is very sensitive to such tensile forces.

Some embodiments as screw-in geometries comprise a convex or concave multi-lobe outer structure, as for example a regular or irregular curve of equal width. A curve of equal width is a closed curve of a constant width. Thereby, the width is defined as the distance between two parallel straight lines which contact the closed curve at opposite sides. The trivial shape of a curve of equal width, specifically the circle shape is ruled out, since it does not permit the transmission of torques. Curve of equal width outer structures of a regular curve of equal width which are symmetrical with respect to an axial rotation about a symmetry angle are preferred. Regular curves of equal width are based on regular polygons with an uneven number of corners. A further advantage of screw-in geometries in the form of a curve of equal width is their manufacturability by way of material-removing methods.

The insertion geometry can be cylindrical, i.e. translationally symmetrical or conical along the axis, i.e. continuously reducing or increasing as a function of the axial position in one region whilst retaining the shape of the peripheral line, or it can also for example have a slightly convex or slightly concave shape in a section parallel to the axis.

The smallest implant diameter of the insertion geometry of the ceramic implant however in all embodiments is at least equal to the core diameter of the thread. In some embodiments of the ceramic implant, the implant diameter of the insertion geometry is at least 10%, 15%, 20%, 25% or 35% greater than the core diameter, in particular it is at least 12%, 14%, 16%, 18%, 20%, 22%, 24%, 26%, 28%, 30% or 32% greater with respect to the thread diameter. The stress distribution in the ceramic implant with an insertion geometry designed as an outer structure and with a comparatively large implant diameter is more favourable than with inner geometries which entail small wall thickness of the ceramic implant and thus favour an increased risk of breakage.

The proximal region is arranged proximally to the intermediate region and thus also proximally to the insertion geometry. In some embodiments, the greatest implant diameter in the proximal region at the most is equal to or smaller than the greatest implant diameter of the insertion geometry. In some embodiments, the greatest implant diameter in the proximal region at the most is equal to the greatest implant diameter in the threaded region and in particular at the most is equal to the greatest thread diameter.

In particular, some embodiments of the ceramic implant, in the proximal region in every section perpendicular to the implant axis have an implant diameter which is smaller than the double of the inner radius of the insertion geometry. The greatest implant diameter of such embodiments of the ceramic implant is then arranged in the intermediate region.

In some embodiments of the ceramic implant, the proximal region has a cylindrical, in particular circularly cylindrical shape. In further embodiments of the ceramic implant, the implant diameter continuously reduces in the proximal direction from the border to the intermediate region. In further embodiments of the ceramic implant, the increase and reduction of the implant diameter alternates, for example such that the implant diameter firstly reduces in the proximal direction from the border to the intermediate region, and then widens again and/or for example it firstly forms a necking in the proximal direction and then a head. Such a shape with a head in the proximal region is particularly suitable for a ceramic implant with a lockball for the attachment element.

In some embodiments, the at least one structure for fastening a single-part or multi-part attachment element is designed as a male which is connectable to an attachment element designed as a female. In some embodiments, the at least one structure for connecting an attachment element comprises a male which is connectable to at least one attachment element designed as a female. Such females and in particular such female systems are known in the state of the art as connection elements for an optionally removable fixation of a dental prosthesis on a male connectable to the female. In such embodiments of the single-part ceramic implant according to the invention, the male is thus a proximal constituent of the ceramic implant, whereas with known two-part implants, usually a male is screwed into the implant anchored in the bone. In particular, in some embodiments of the ceramic implant, the proximal region comprises a male, which is compatible with a commercially available male-female system such as a Locator male for a Locator female system, for example the Novaloc™ female system or a lockball male for a lockball female system, for example the Pro-Snap female system of Cendres Metaux.

Advantageously, an attachment element can be applied onto embodiments of the ceramic implant with a lockball at each and any rotational position. Thus the dental surgeon can screw in the threaded region until the axial height of the implanted implant is optimally set, without considering the rotational position. A ceramic implant equipped with a lockball in the proximal region thus places less demands on the implantation accuracy.

In some embodiments of the ceramic implant, the proximal region, or rather the implant axis in the proximal region is at an angle of up to 25% relative to the distally adjacent insertion geometry, or rather to the implant axis through the insertion geometry. In some embodiments of the ceramic implant, a proximal part is designed for example as an angled stem.

Some embodiments of the ceramic implant in the proximal region have structures such as ribs for example or the like, for the additional fastening or rotational locking of one of the parts of the single-part or multi-part attachment element, or grooves or the like, for example for receiving a snap element, for example a snap ring or a seal.

A further aspect of the invention relates to a dental implant system comprising a ceramic implant and additionally comprising a single-part attachment element or at least a part of a multi-part attachment element, in particular a retention element. The retention element in some embodiments is a female on which or by way of which the at least one structure in the proximal region can be fastened on the implant.

A multi-part attachment element comprises or consists for example of a retention element, in particular of a female, and of a dental prosthesis such as a crown or a denture. In some embodiments of the dental implant system, it comprises the ceramic implant and at least one single-part or multi-part female.

In some embodiments of such a multi-part attachment element, the retention element is permanently or releasably connectable to the proximal region of the ceramic implant and/or the retention element is permanently or releasably connectable to the prosthesis. In some embodiments of the retention element, it is multi-part, in other embodiments it is of one part. In some embodiments, the retention element is designed as a single part or multi-part female for a lockball.

A further subject matter of the invention is a set with at least one ceramic implant and an insertion tool. Optionally, the set comprises more than one ceramic implant, in particular a ceramic implant system. The insertion tool cooperates with the insertion geometry of the at least one ceramic implant. The set optionally additionally comprises a single-part or multi-part attachment element such as for example retention elements, other prosthetic parts, or carrier elements for prostheses such as dentures, bridges, crowns and the like. The set comprises at least one attachment element or at least a part of the attachment element, wherein these are provided for the direct fastening on the ceramic implant.

The ceramic implant, the ceramic implant system or the dental implant system and the set can be present in a sterile package.

BRIEF DESCRIPTION OF THE DRAWINGS

Embodiment examples of the invention are hereinafter described in more detail by way of figures. The invention is not limited to the combination of features of the invention which are represented in the figures. In particular, it is also possible to combine features which are specifically disclosed for a first of the three regions, the threaded region, intermediate region, and proximal region of the ceramic implant, with all disclosed embodiments of the two other regions and not only with that or those embodiments of the other regions, which for example are described in combination with the first region or are represented in the figures. The figures are not necessarily true to scale. The same reference numerals indicate the same or analogous elements.

DETAILED DESCRIPTION OF THE INVENTION

Figure 1A:
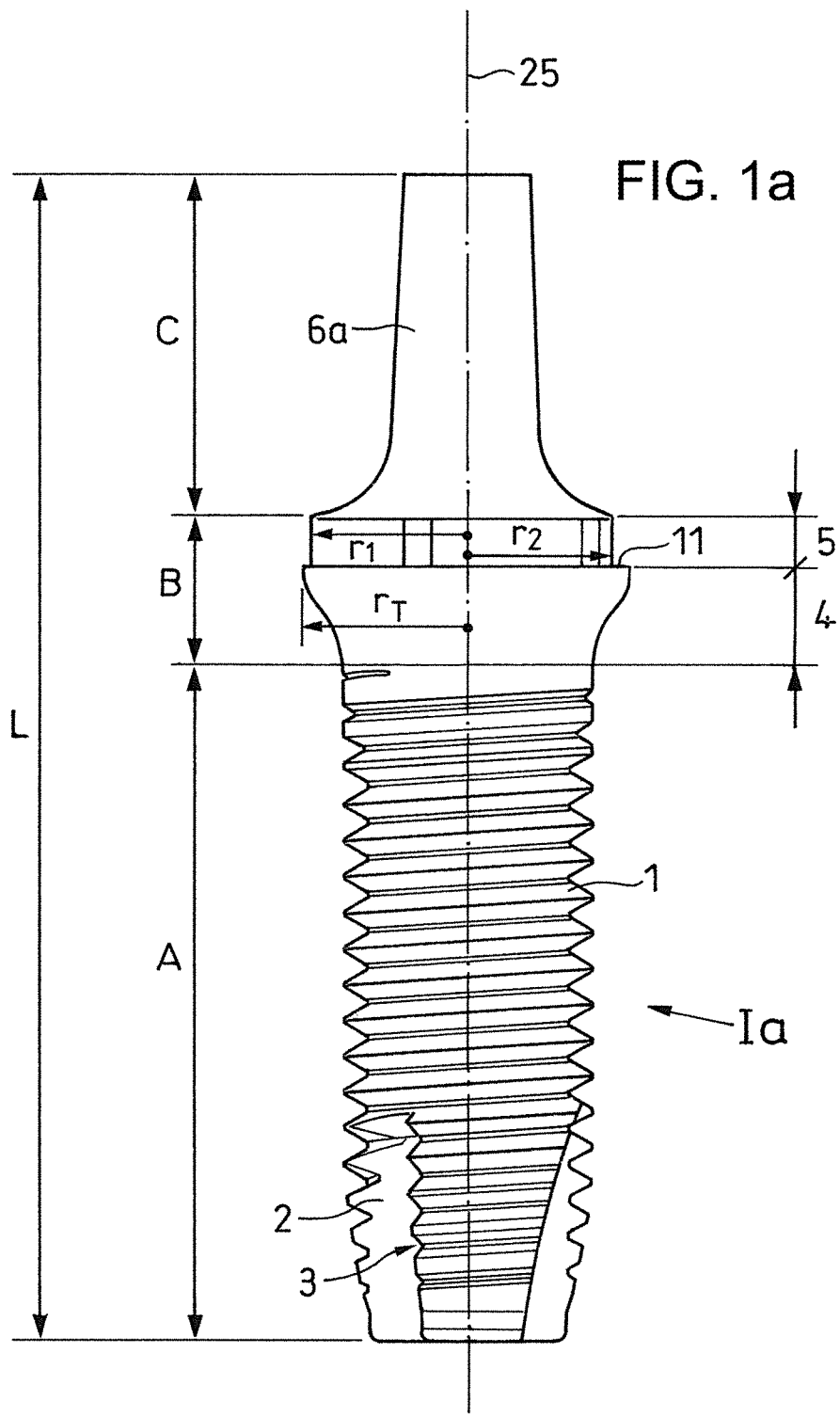
FIGS. 1a and b are elevation views that show exemplary embodiments 1a and 1b of a ceramic implant with a widening zone.
Figure 1B:
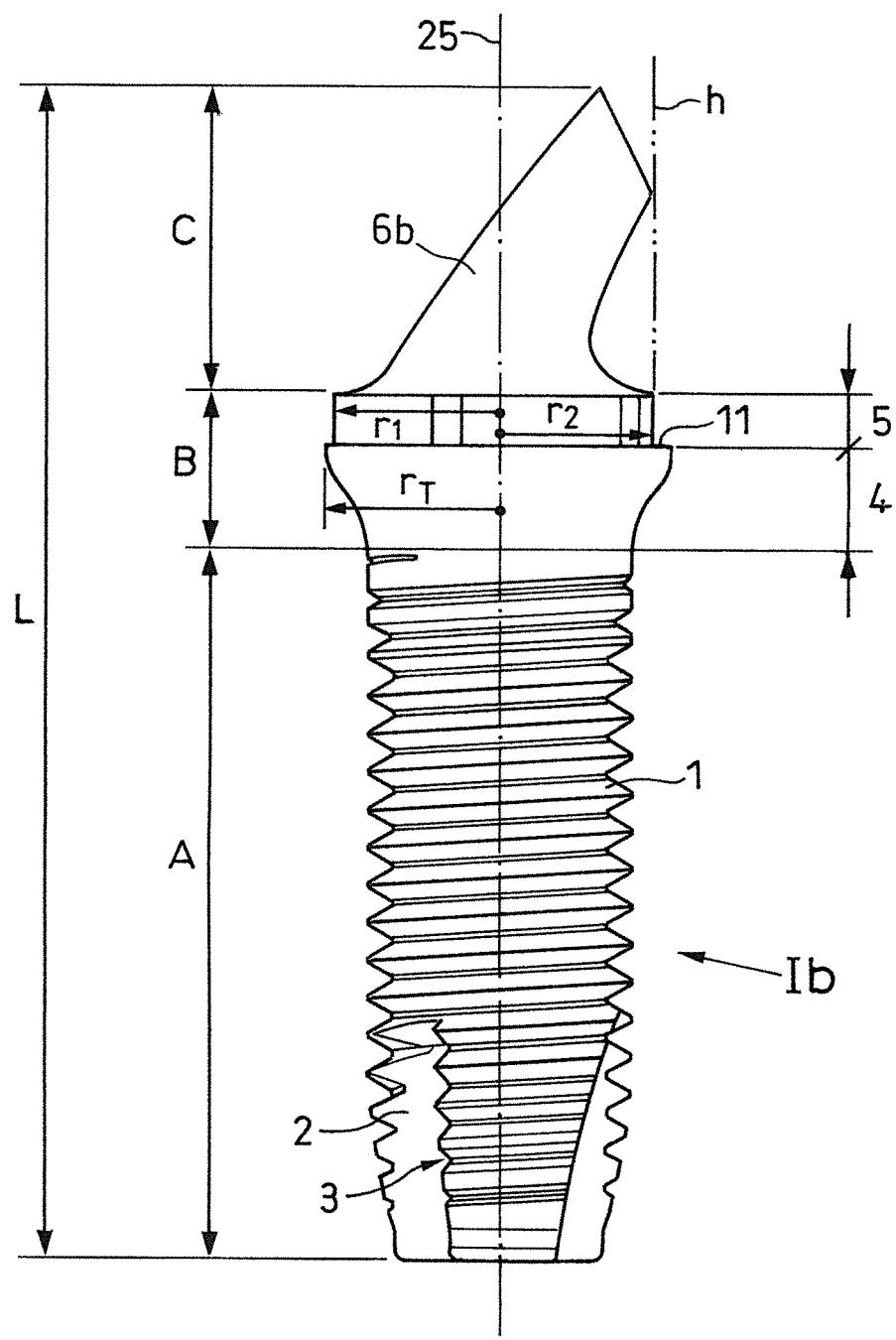
Figure 2:
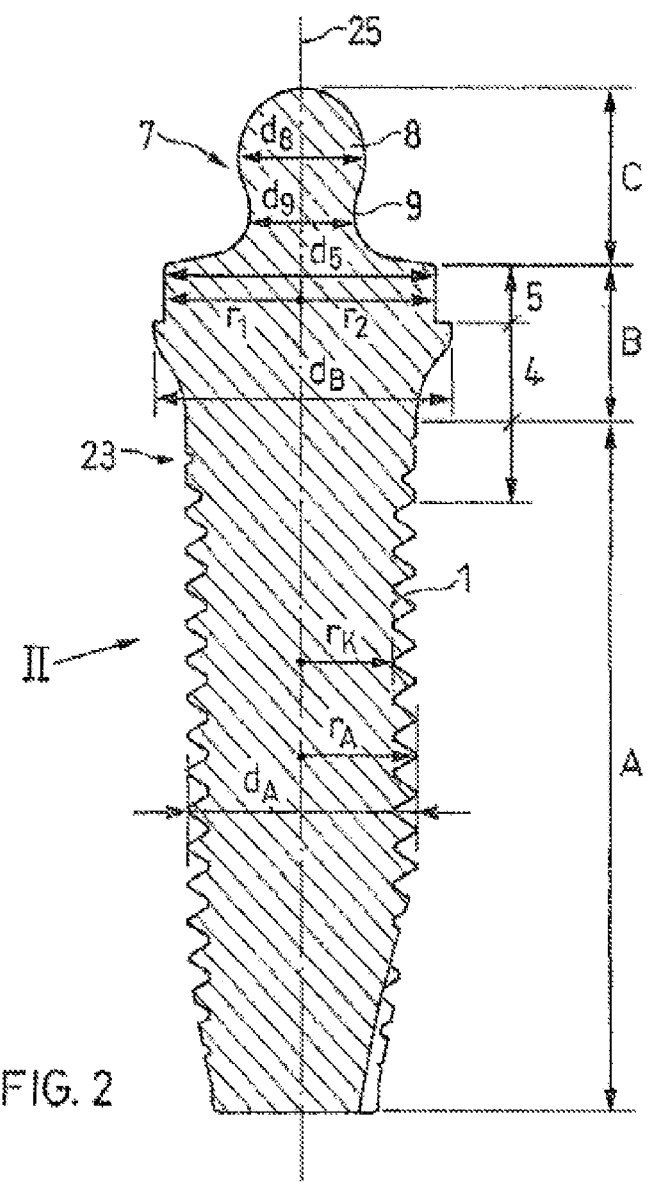
FIG. 2 is a sectional elevation view that shows a longitudinal section through an exemplary ceramic implant II.

FIGS. 1a and 1b show a schematic view of the exemplary embodiments 1 and 1b of the ceramic implant and FIG. 2 shows a schematic longitudinal section through the exemplary embodiment II of the ceramic implant with an axial implant length L, a distal enossal threaded region A, a gingival intermediate region B, a proximal region C and an implant axis 25.

The enossal threaded region A of the exemplary ceramic implants Ia, Ib and II is provided with a thread 1 which optionally comprises at least one groove 2 and likewise optionally a thread run-out 23. The groove 2 opens to the distal implant face side. The intermediate region B in this exemplary embodiment comprises a widening zone 4 and an insertion geometry 5.

The proximal region C is provided with at least one structure for fastening a single-part or multi-part attachment element. The exemplary ceramic implants Ia, Ib and II differ only in the proximal region C.

With the exemplary embodiment Ia represented in FIG. 1a, the proximal region C is designed as a conical stem 6a for receiving an attachment element. The middle axis of the stem 6a of the embodiment 1a corresponds to the implant axis 25 in the intermediate region B and the enossal threaded region A.

With the exemplary embodiment Ib represented in FIG. 1b, the proximal region C is designed as an angled stem 6b. In some embodiments, the stem is maximally angled to such an extent that the stem does not project beyond the inner radius $r_2$ of the non-rotationally-symmetrical outer structure of the insertion geometry 5. This is represented in FIG. 1b by the auxiliary line h. Advantageously, with embodiments with an angled stem which does not project out beyond the inner radius of the non-rotationally-symmetrical outer structure of the insertion geometry 5, this insertion geometry is accessible from the proximal side for the same insertion tool, as for a corresponding embodiment of the ceramic implant for example with a conical stem, whose middle axis corresponds to the implant axis 25 in the intermediate region B and in the enossal thread region A.

Figure 3A:
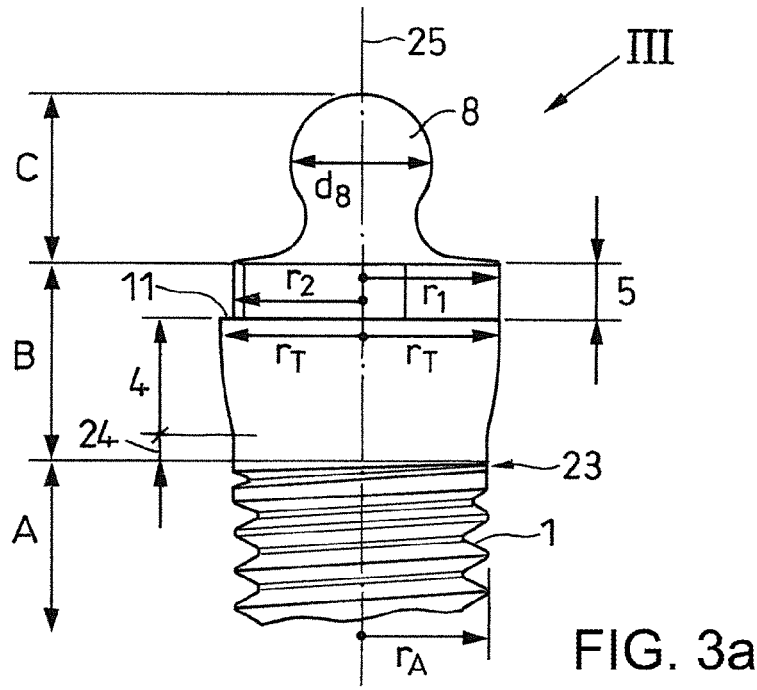
FIGS. 3a-3b are elevational views showing one embodiment example of a ceramic implant system containing exemplary ceramic implants III (FIG. 3a) and IV (FIG. 3b) with an equal non-rotationally symmetrical outer geometry of the insertion geometry and different outer radius of the thread.
Figure 3B:
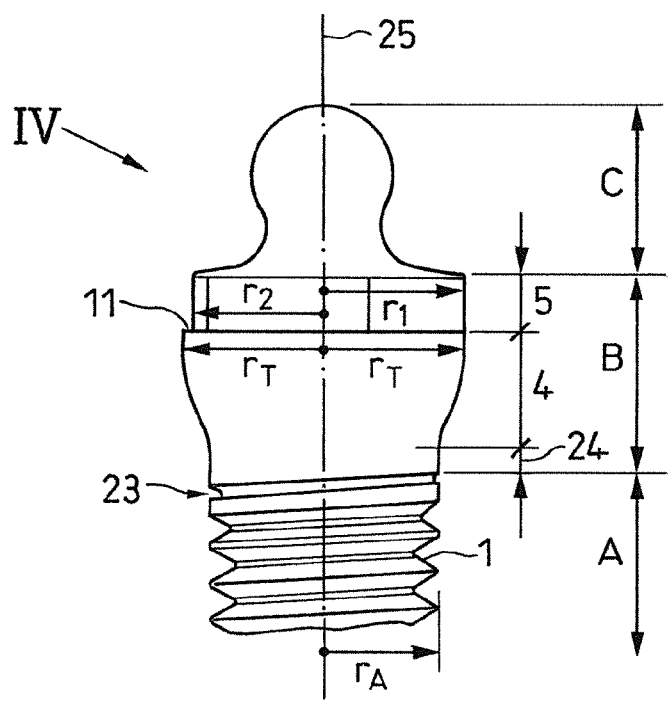

With the exemplary embodiment II represented in FIGS. 2 and 3, the proximal region is designed as a lockball 7 for receiving an attachment element and comprises a head 8 and a necking 9.

The threaded region A of the exemplary ceramic implants Ia, Ib and II comprises a self-cutting thread 1 with cutting edges 3 of the thread 1 on the groove 2. The groove 2 as the case may be can accommodate bone material cut away on screwing in. Whereas the represented exemplary groove 2 runs in an axial manner, in other embodiments it can run helically for example instead of axially.

Implant diameters $d_A$, $d_B$, $d_5$, $d_8$ and $d_9$ are drawn in FIG. 2. Thereby, $d_A$ and $d_B$ indicate exemplary implant diameters in the threaded region A and in the intermediate region B of the ceramic implant. $d_5$ indicates an exemplary implant diameter of the insertion geometry 5 in the region B. In the intermediate region B, $r_1$ specifies an outer radius and $r_2$ an inner radius of the non-rotationally-symmetrical outer structure of the insertion geometry 5. In the proximal region C, $d_8$ indicates the diameter of a round head 8 and $d_9$ a waist, thus the smallest diameter of a necking 9 of the proximal region C.

FIG. 2 shows that every implant diameter in the intermediate region B, such as the implant diameter $d_B$ draw in by way of example, is at least equal to or larger than the double of the core radius $r_K$ of the thread 1 in the threaded region A. Since the insertion geometry 5 is arranged in the intermediate region B, also every implant diameter $d_5$ of the insertion geometry 5 must be larger than or equal to the double of the core radius of the thread $r_K$ in the threaded region A. In some embodiments, the double of the inner radius $r_2$ of the non-rotationally-symmetrical outer structure of the insertion geometry 5 is at least equal to the double of the core radius of the thread $r_K$. In the exemplary embodiments represented in FIG. 1 and in FIG. 2, the core radius $r_K$ and the outer radius $r_A$ are constant over the larger part of the axial length of the thread 1 and the core radius rK and the outer radius rA reduce in the distal direction towards the distal face side of the ceramic implant, whilst a thread run-out 23, in which the core diameter $r_K$ increases in the proximal direction whist the outer radius $r_A$ remains unchanged, is arranged at the proximal end of the threaded region A.

The exemplary embodiments I and II of the ceramic implant have an embodiment with a tulip-shaped widening zone 4. The implant diameter, beginning at the distal end of the widening zone at the border to the threaded region A widens in the proximal region in an exemplary firstly convex and the concave S-curve. The insertion geometry 5 is arranged adjacent the widening zone 4 in the proximal direction and here has a somewhat reduced implant diameter. A shoulder 11 is formed by way of this at the proximal end of the widening zone 4 or at the distal end of the insertion geometry. This shoulder 11 has an advantageous stop effect on an insertion tool which is applied from the proximal side onto the insertion geometry 5.

The axial total length L of some embodiments of the ceramic plate for example lies in a region of 10 to 25 mm and in particular in a region with a lower limit of a value between 11 and 18 mm and an upper limits of a value between 19 and 24 mm.

The lengths mentioned hereinafter in each case relate to the axial length of an implant region of some embodiments of the ceramic implant, wherein specific lengths of an implant region can be freely combined with specific lengths of another implant region of the ceramic implant. The distal enossal threaded region A for anchoring the ceramic implant in the bone for example has a length in a region of 8 to 16 mm and in particular in a region with a lower limit of 9, 10, 11 or 12 mm and an upper limit of 11, 12 13, 14 or 15 mm. The intermediate region B for example has a length in a region of 1 to 4 mm and in particular in a region with a lower limit of 1, 1.5 or 2 mm and an upper limit of 2.5, 3 or 3.5 mm. The proximal region A with at least one structure for fastening a single-part or multi-part attachment element for example has a length in a region of 1.5 to 6 mm and in particular in a region with a lower limit of 1.5, 2.0, 2.5 or 3.0 mm and an upper limit of 2.5, 2.75, 2.9, 3.0, 3.1, 3.25, 3.5, 4, 4.5 or 5 mm.

Some exemplary embodiments of a ceramic implant system for example comprise ceramic implants with an axial length of the distal enossal region A of 8 to 16 mm or 9 to 14 mm or 10.5 to 12 mm, in particular 11.25 mm, with an axial length of the intermediate region B of 2 to 3 mm, in particular 2.5 mm and with an axial length of the proximal region C of 2 to 3.5 mm, in particular 2.5 to 3 mm or 2.7 to 2.8 mm.

The axial length of the insertion geometry 5 in some embodiments is in the region of 0.5 to 1.5 mm, in particular of 0.8 to 1.2 mm or 0.89 to 1.1 mm.

Some embodiments of the ceramic implant with a lockball male have an axial length of the threaded region A of a value between 7 mm and 13 mm, in particular of 8.5 mm, 10 mm and 11.5 mm, of the intermediate region B for gingiva heights of for example 2 mm to 5 mm, in particular 2.0 mm, 2.5 mm, 3.0 mm, 3.5 mm, 4.0 mm or 4.5 mm and of the proximal region of for example 2.9 mm to 3.9 mm, in particular 3.4 mm with the double of the core radius $r_K$ of the thread of for example 3.9 to 5 mm, in particular 4.1 to 4.7 mm. In the intermediate region, some embodiments have an axial length of the insertion geometry of 0.4 to 1.4 mm, in particular 0.7 to 1.1 mm and of the widening zone of 1.5 to 2.5 mm, in particular 1.8 to 2.2 mm or another combination which results in the desired axial length of the intermediate region for a corresponding gingiva height.

Some embodiments of the ceramic implant system alternatively or additionally to the different embodiments of the ceramic implant described above additionally have embodiments with which the thread diameter or the implant diameter differs at the proximal end of the threaded region. The implant diameter at the proximal end of the threaded region for example measures between 3 and 4.5 mm or in particular between 3.5 mm and 4 mm.

FIG. 3 shows exemplary embodiments III and IV of the ceramic implant in schematic part views with the proximal part C and the intermediate region B, comprising an insertion geometry 5, an optional widening zone 4 and an optional distancing zone 24 as well as with a threaded region A which is not completely shown and of which a distal part of the thread and the distal end of the threaded region A are not shown.

The proximal part C of the embodiments III and IV is designed in an identical manner and comprises a lockball, for example a lockball male for a commercially available female.

The insertion geometry 5 of both embodiments III and IV which is adjacent the distal end of the proximal part also has an equal non-rotationally-symmetrical outer structure here for example a curve of equal width with the same outer radii $r_1$ and the same inner radii $r_2$.

In contrast, in the two exemplary embodiments of the ceramic implant III and IV the double of the outer radius $r_A$ of the thread 1 is different and therefore these two embodiments also have a different implant diameter at the proximal end of the thread. This difference for example is less than 1 mm, in particular 0.1 mm to 0.8 mm or 0.2 mm to 0.6 mm or 0.3 to 0.5, for example 0.4 mm.

The outer radii $r_1$ of the screw-in geometries 5 of the embodiments III and IV represented by way of example are equal to the radius $r_T$ of the widening zone 4 at its proximal end. The inner radii r2 of the non-rotationally-symmetrical outer structure of the screw-in geometries 5 of the embodiments III and IV represented by way of example are for example 0.025 mm to 0.3 mm smaller than the outer radii $r_1$, in particular 0.05 mm to 0.15 mm or 0.07 to 0.1 mm smaller than the outer radii $r_1$ or than the radius $r_T$ at the proximal end of the widening zone 4. The outer radius $r_1$ of the outer structure of the insertion geometry for example measures 1.5 mm to 2.5 mm, in particular 1.8 mm to 2.2 mm. A diameter $d_5$ of the insertion geometry for example measures 3.5 to 5 mm, in particular 3.8 mm to 4.7 mm or 4 mm to 4.5 mm.

The two embodiment examples of the ceramic implant which are represented in FIG. 3 are contained in an exemplary ceramic implant system, with which the different design of the widening zones 4 is matched to the different thread diameters such that the widening zone of both embodiments II and IV at their distal end has an implant diameter which is equal to the respective implant diameter at the proximal end of the threaded region or equal to the double of the outer radius $r_A$ of the thread and that the widening zone at its proximal end has an implant diameter which is equal to the double of the outer radius $r_1$ of the same outer structure of the insertion geometry 5.

The exemplary embodiments III and IV of the exemplary ceramic implant system additionally to the widening zone 4 comprise an optional distancing zone 24 in intermediate region B, and this distancing zone is arranged between the proximal end of the threaded region A and the distal end of the widening zone 4. In the distancing zone, the implant diameter does not widen in comparison to the implant diameter at the proximal end of the threaded region and in particular, as in the embodiments III and IV is equal to the double of the outer radius $r_A$ of the thread.

Figure 4A:
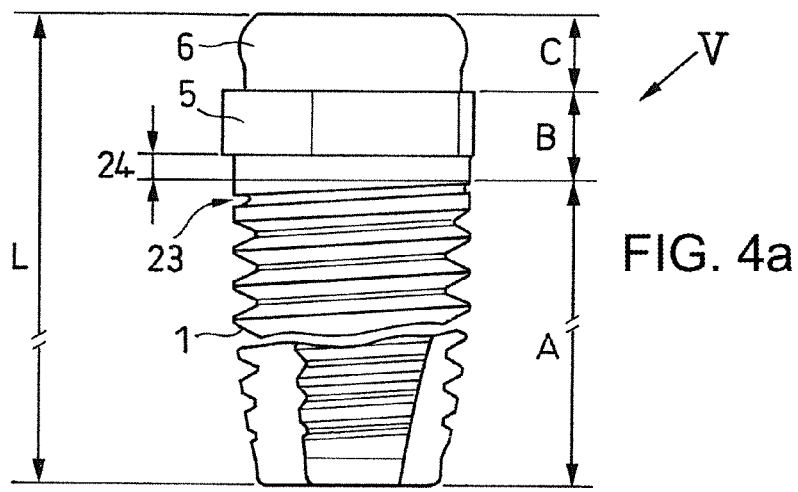
FIGS. 4a-4c are elevational views showing embodiments of the ceramic implant system with three embodiments V (FIG. 4a), VI (FIG. 4b) and VII (FIG. 4c) of the ceramic implant with the same non-rotationally-symmetrical outer structure of an insertion geometry with a different axial length.
Figure 4B:
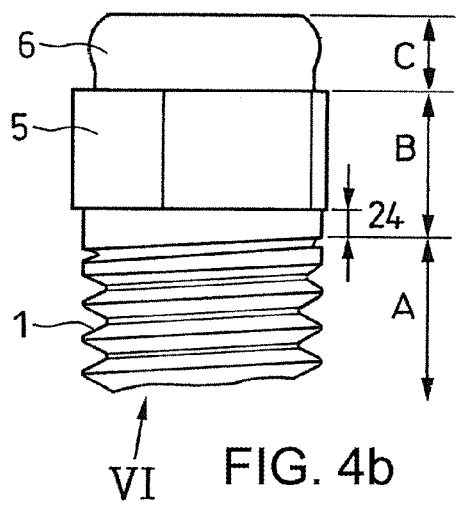
Figure 4C:
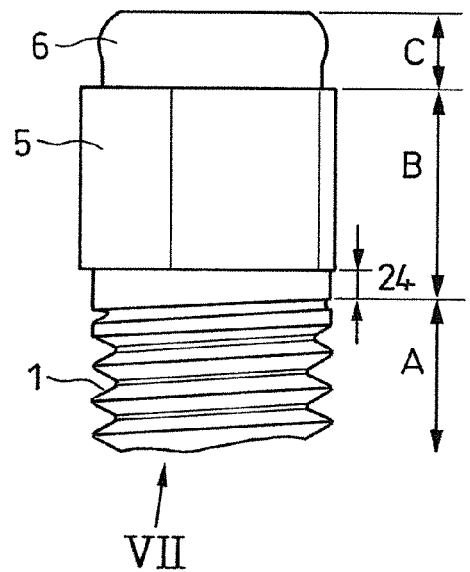

FIG. 4 shows schematic part views of three further exemplary ceramic implants V which comprise a locator male in the proximal region. Such and optionally further embodiment examples of the ceramic implant are contained in a ceramic implant system for example.

Some embodiments of the ceramic implant with a locator male have an axial length of the threaded region A of for example 8 to 12 mm, in particular of 8.5 mm, 9.0 mm, 9.5 mm or 10.0 mm to 10.5 mm, 11.0 mm or 11.5 mm, an axial length of the intermediate region B for different gingiva heights of for example 2 mm to 5 mm, in particular of 2.5 mm, 3.0 mm or 3.5 mm to 3.5 mm, 4.0 mm or 4.5 mm and of the proximal region of for example 2.5 to 4.5, in particular 3.0 to 4.0 mm. The implant diameter of these embodiments in the proximal threaded region for example measures between 3 mm and 4.5 mm, in particular 3.5 mm to 4.0 mm.

The intermediate region B in some embodiments such as for example of the ceramic implants V, VI and VII in FIG. 4 without a widening zone and without a distancing zone are designed as a non-rotationally-symmetrical insertion geometry over its entire axial length. The axial lengths of the screw-in geometries 5 are between 2 and 5 mm, those of the drawn one of the implants V, VI and VII for example measure 2.5 mm, 3.5 mm and 4.5 mm. In other embodiments which are not drawn, the intermediate length is not designed as an insertion geometry over the entire length and additionally comprises a distancing zone and/or a widening zone.

With the embodiments V, VI and VII of the ceramic implants shown by way of example, the outer radius of the insertion geometry 5 is larger than the outer radius of the thread.

Figure 5:
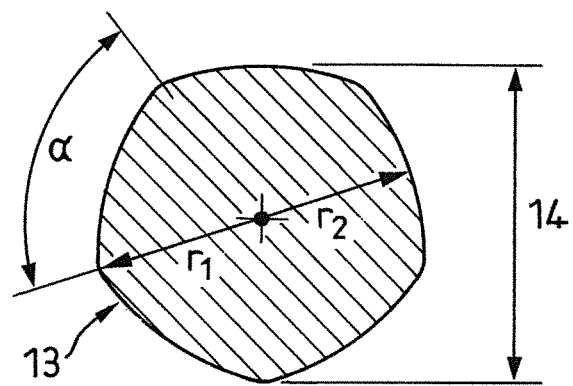
FIG. 5 is a sectional plan view that shows a cross section through an exemplary embodiment of the insertion geometry.

FIG. 5 shows a cross section through the insertion geometry 5 of the exemplary embodiments of the ceramic implant in the FIGS. 1 to 5. This insertion geometry is designed as a non-rotationally-symmetrical outer structure for example in the form of a curve of equal width 13.

Of course, the embodiment of the insertion geometry 5 which is represented in FIG. 5 can also be used for embodiments of the ceramic implant other than the embodiment examples mentioned above and of course the represented embodiment examples of the ceramic implant could likewise be designed with another non-rotationally-symmetrical outer structure as an insertion geometry, for example with another curve of equal width or with an outer polygon etc.

The non-rotationally-symmetrical outer structure of the insertion geometry 5 which is represented by way of example in FIG. 5 is a curve of equal width 13 which is a regular curve of equal width based on a regular pentagon with an angle α of 72° and by definition with a constant width 14. The magnitude of the constant width 14 for example lies in a region with a lower limit of 3, 3.25, 3.5, 3.75, 4, 4.25, 4.5, 4.75 or 5.0 mm and an upper limit in a region of 4.5, 4.75, 5.0, 5.5, 5.75 or 6 mm and in particular lies in a region of 3.5 to 5.5 mm.

In other embodiments of the insertion geometry 5 in the intermediate region B and which are not drawn, the non-rotationally-symmetrical outer contour for example is an irregular curve of equal width or an outer polygon. The implant diameter of the insertion geometry on embodiments with an outer polygon for example measures 3.5 to 6 mm, in particular 4 to 5 mm in some embodiments.

FIGS. 1a, 1b, 2 and 3 show that the insertion geometry 5 in the exemplary embodiments Ia, Ib and II to IV is set back in comparison to the distally adjacent widening zone 4, which means that the outer radius $r_1$ of the non-rotationally symmetrical insertion geometry is smaller or in particular equal to the outer radius $r_T$ of the distally adjacent widening zone 4, and the inner radius $r_2$ of the insertion geometry 5 is smaller than the outer radius $r_T$ of the distally adjacent widening zone 4. Thus in these and some further embodiments, the implant diameter $d_5$ of the set-back insertion geometry 5 is smaller than the implant diameter of the implant region distally adjacent the insertion geometry 5, such as for example of a distally adjacent widening zone 4, of a distally adjacent distancing zone 24 or of a distally adjacent threaded region A.

In other embodiments of the ceramic implant, the insertion geometry 5 projects with respect to an implant region distally adjacent the insertion geometry 5, such as for example with respect to a distally adjacent widening zone 4, a distally adjacent distancing zone 24 or a distally adjacent thread region A. In particular, in such embodiments of the ceramic implant, the implant diameter $d_5$ of the insertion geometry 5 is greater and in particular the outer radius $r_1$ of the outer structure of the insertion geometry 5 is greater than the diameter or the greatest radius in a section perpendicular to the axis through the ceramic implant, directly distally to the insertion geometry at the proximal end for example of the optional widening zone 4 or of the optional distancing zone 24 or of the threaded region A. The embodiments V, VI and VII of the ceramic implant represented in FIG. 4 have such an insertion geometry projecting with respect to the distally adjacent distancing zone.

Figure 6:
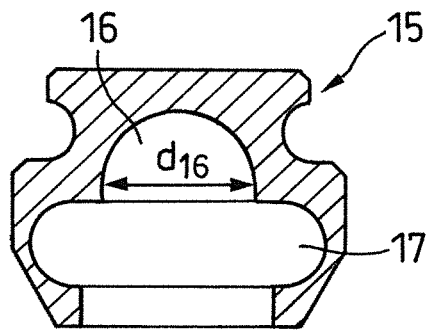
FIG. 6 is a sectional elevation view shows an exemplary embodiment of an attachment element for a ceramic implant with a lockball.

FIG. 6 shows a cross section through an exemplary embodiment of a part 15 of a multi-part attachment element of a dental implant system. The part 15 is retention element which is fastenable in the proximal region C of the ceramic implant and which is connectable to at least one further part of the attachment element and e.g. holds a prosthesis such as a bridge, denture or dental crown.

The retention element 15 represented by way of example in FIG. 6 is designed as a female and comprises a semi-spherical cavity 16 for receiving a head 8 of the lockball 7, wherein the diameter $d_{16}$ of the cavity is adapted to the head diameter $d_8$.

In the exemplary embodiment of the attachment element according to FIG. 6, the retention element 15 designed as a female comprises a recess 17 for a snap element, for example for a snap ring which in particular is inserted in the region of the necking 9 of the ceramic implant between the surface of the ceramic implant and the inner wall of the male, into the recess 17. The snap element contains silicone and, in particular, is a silicone ring.

The invention claimed is:

1. A single-piece ceramic dental implant, comprising
a distal enossal threaded region, in which a thread is arranged, with a core radius and an outer radius of the thread,
an intermediate region, in which a proximally accessible insertion geometry for screwing the threaded region into a bone tissue is arranged, wherein the insertion geometry is designed as a non-rotationally-symmetrical outer structure,
and a proximal region with at least one structure for fastening a single-part or multi-part attachment element, a transition between the intermediate region and the proximal region being formed by a circumferential edge or shoulder,
wherein an implant diameter in every section perpendicular to an implant axis in the intermediate region and thus also through the insertion geometry arranged in the intermediate region is equal to or larger than the double of the core radius of the thread;
and wherein the non-rotationally-symmetrical outer surface has a translational symmetry with respect to a translation parallel to the implant axis, or wherein the insertion geometry has a reduced diameter in a coronal direction whereby the insertion geometry has a conical shape tapering toward the coronal direction.

2. The ceramic implant according to claim 1, with the non-rotationally-symmetrical outer structure of the insertion geometry, comprising an outer radius and an inner radius, wherein the inner radius of the insertion geometry is equal to or larger than the core radius of the thread.

3. The ceramic implant according to claim 2, wherein a difference between the outer radius and the inner radius of the non-rotationally-symmetrical outer structure of the insertion geometry is between 0.13 mm and 0.3 mm.

4. The ceramic implant according to claim 2, wherein the intermediate region additionally proximally of the threaded region and distally of the insertion geometry has a tulip-shaped widening zone, wherein an implant diameter at a distal end of the widening zone is equal to or larger than the double of the outer radius of the thread, and at a proximal end of the widening zone is larger than at the distal end of the widening zone.

5. The ceramic implant according to claim 4, wherein the outer radius of the insertion geometry is smaller than or equal to an outer radius of the tulip-shaped widening zone at the proximal end of the widening zone.

6. The ceramic implant according to claim 2, wherein the outer radius of the insertion geometry is equal to or larger than the outer radius of the thread.

7. The ceramic implant according to claim 2, wherein an implant diameter in every section perpendicular to an implant axis in the proximal region is equal to or smaller than the double of the inner radius of the insertion geometry.

8. The ceramic implant according to claim 1, wherein the insertion geometry is an outer hexagon, outer octagon, or outer bi-hexagon or a convex or concave multi-lobe structure.

9. The ceramic implant according to claim 8, wherein the insertion geometry is a concave and/or a regular or irregular curve of equal width having the same outer radii and the same inner radii.

10. The ceramic implant according to claim 1, wherein the at least one structure in the proximal region for fastening the single-part or multi-part attachment element is designed as a male for connection to a female, or comprises a male for connection to a female or wherein the proximal region is designed as a stem or as an angled stem.

11. A ceramic implant system comprising at least two ceramic implants according to claim 1 with an equal non-rotationally symmetrical outer geometry of the insertion geometry, wherein the ceramic implants of the ceramic implant system differ at least by way of an axial length of the insertion geometry and/or in the design of at least one other implant region.

12. A dental implant system comprising at least one ceramic implant according to claim 1 or a ceramic implant system according to claim 11 and additionally comprising at least one single-part attachment element or at least one part of a multi-part attachment element.

13. The dental implant system according to claim 12, wherein the at least one single-part or the at least one part of the multi-part attachment element is connectable to the ceramic implant via a snap connection or a press fitting.

14. The dental implant system according to claim 12, additionally comprising a snap element.

15. The dental implant system according to claim 14, wherein the snap element is designed as a snap ring.

16. The dental implant system according to claim 14, wherein the snap element contains silicon.

17. A set comprising a dental implant system according to claim 12, additionally comprising an insertion tool for the ceramic implant.

18. The dental implant system according to claim 12, wherein the at least one ceramic implant or the ceramic implant system additionally comprises a retention element.

19. A set comprising a ceramic implant according to claim 1 or a ceramic implant system according to claim 11 additionally comprising an insertion tool for the ceramic implant.

20. The ceramic implant system according to claim 11, wherein the ceramic implants of the ceramic implant system differ at least in the design of at least one of the enossal threaded region, of the proximal region, of the intermediate region comprising at least one of a widening zone and a distancing zone distally of the insertion geometry.

\* \* \* \* \*